US006266547B1

(12) United States Patent
Walker et al.

(10) Patent No.: US 6,266,547 B1
(45) Date of Patent: Jul. 24, 2001

(54) NASOPHARYNGEAL AIRWAY WITH REFLECTANCE PULSE OXIMETER SENSOR

(75) Inventors: Steven C. Walker, Olmos Park; John M. Shepherd, Fort San Antonio; John G. Alexander, Plano, all of TX (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/389,354

(22) Filed: Sep. 3, 1999

Related U.S. Application Data

(60) Provisional application No. 60/101,143, filed on Sep. 18, 1998, and provisional application No. 60/099,579, filed on Sep. 9, 1998.

(51) Int. Cl.[7] .......................................................... A61B 5/00
(52) U.S. Cl. ............................................ 600/344; 600/323
(58) Field of Search .................................. 600/310, 322, 600/323, 340, 344, 324–8, 331–2, 334, 337, 339, 341; 128/200.26, 200.24, 203.13, 204.18, 205.11, 207.18

(56) References Cited

U.S. PATENT DOCUMENTS

| 3,908,665 | 9/1975 | Moses . |
| 4,270,531 | 6/1981 | Blachly et al. . |
| 4,495,945 | 1/1985 | Liegner . |

(List continued on next page.)

FOREIGN PATENT DOCUMENTS

| 4 42 260A1 | 5/1996 | (DE) . |
| WO 86/00207 | 1/1986 | (WO) . |
| WO 90/01293 | 2/1990 | (WO) . |

(List continued on next page.)

OTHER PUBLICATIONS

Sheridan et al., "Intraoperative Reflectance Oximetry in Burn Patients," Journal of Clinical Monitoring, Jan. 1995, vol. 11 (1): 32–34.

Faisst et al., "Intrapartum Reflectance Pulse Oximetry: Effects of Sensor Location and Fixation Duration on Oxygen Saturation Readings," Journal of Clinical Monitoring, Sep. 1997, vol. 13 (5): 299–302.

Izumi et al., "Accuracy and Utility of a New Reflectance Pulse Oximeter for Fetal Monitoring During Labor," Journal of Clinical Monitoring, Mar. 1997, vol. 13 (2): 103–108.

Hayes, et al., "Quantitative Investigation of Artefact in Photoplethysmography and Pulse Oximetry for Respiratory Exercise Testing," Aug. 29, 1997, Web Article: HTTP://WWW.LUT.AC.UK.DEPARTMENTS/EL/RESEARCH/OPTICS/PPGRAPHY/PAPER2.htm.

Anonymous, "Photon Flow For Pulse Oximetry," Sep. 15, 1995, Web Article: HTTP://WWW.LLNL.GOV/BBRP/HEALTHCARE/PROJECTS.PFPULSEOXIM.html.

Faisst, et al., "Reflectance Pulse Oximetry in Neonates," European Journal of Obsterics & Gynecology and Reproductive Biology, Aug. 1995, vol. 61, pp. 117–122.

(List continued on next page.)

Primary Examiner—Eric F. Winakur
(74) Attorney, Agent, or Firm—Elizabeth Arwine; Charles H. Harris

(57) ABSTRACT

A combined nasopharyngeal airway and pulse oximeter sensor capable of monitoring the posterior pharynx, posterior soft palate or nasal mucosa is disclosed. The nasopharyngeal airway includes a thickened wall section over approximately one-third of its circumference. Pulse oximeter sensor elements may be embedded in the airway. The pulse oximeter sensor elements may include a light source, which preferably emits light at wavelengths around 660 nm (red) and around 940 nm (near infrared), and a light detector. The pulse oximeter sensor elements may be connected to a pulse oximeter monitor (spectrophotometer) or other external device for analysis.

20 Claims, 1 Drawing Sheet

U.S. PATENT DOCUMENTS

| | | |
|---|---|---|
| 4,586,513 | 5/1986 | Hamaguri . |
| 4,621,643 | 11/1986 | New, Jr. et al. . |
| 4,624,572 | 11/1986 | Van Den Bosch . |
| 4,651,746 | 3/1987 | Wall . |
| 4,676,240 | 6/1987 | Gardy . |
| 4,700,708 | 10/1987 | New, Jr. et al. . |
| 4,796,636 | 1/1989 | Branstetter et al. . |
| 4,830,014 | 5/1989 | Goodman et al. . |
| 4,854,699 | 8/1989 | Edgar, Jr. . |
| 4,859,057 | 8/1989 | Taylor et al. . |
| 4,865,038 | 9/1989 | Rich et al. . |
| 4,867,557 | 9/1989 | Takatani et al. . |
| 4,880,304 | 11/1989 | Jaeb et al. . |
| 4,890,619 | 1/1990 | Hatschek . |
| 5,040,539 | 8/1991 | Schmitt et al. . |
| 5,069,214 | 12/1991 | Samaras et al. . |
| 5,090,410 | 2/1992 | Saper et al. . |
| 5,193,544 * | 3/1993 | Jaffe ...................................... 600/323 |
| 5,203,329 | 4/1993 | Takatani et al. . |
| 5,205,281 | 4/1993 | Buchanan . |
| 5,217,012 | 6/1993 | Young et al. . |
| 5,246,003 | 9/1993 | Delonzor . |
| 5,282,464 | 2/1994 | Brain . |
| 5,329,922 | 7/1994 | Atlee, III . |
| 5,355,874 | 10/1994 | Bertram . |
| 5,357,954 | 10/1994 | Shigezawa et al. . |
| 5,361,757 | 11/1994 | Smith et al. . |
| 5,413,101 | 5/1995 | Sugiura . |
| 5,417,207 | 5/1995 | Young et al. . |
| 5,494,032 | 2/1996 | Robinson et al. . |
| 5,595,176 | 1/1997 | Yamaura . |
| 5,596,986 | 1/1997 | Goldfarb . |
| 5,619,992 | 4/1997 | Guthrie et al. . |
| 5,638,593 | 6/1997 | Gerhardt et al. . |
| 5,673,693 | 10/1997 | Solenberger . |
| 5,678,544 | 10/1997 | Delonzor et al. . |
| 5,715,816 | 2/1998 | Mainiero et al. . |
| 5,743,261 | 4/1998 | Mainiero et al. . |
| 5,755,226 | 5/1998 | Carim et al. . |
| 5,797,841 | 8/1998 | Delonzor et al. . |
| 5,800,349 | 9/1998 | Isaacson et al. . |
| 5,817,009 | 10/1998 | Rosenheimer et al. . |
| 5,839,439 | 11/1998 | Nierlich et al. . |
| 5,954,050 * | 9/1999 | Christopher .................... 128/204.23 |
| 5,983,120 * | 11/1999 | Groner et al. ...................... 600/310 |
| 5,991,648 | 11/1999 | Levin . |

FOREIGN PATENT DOCUMENTS

| | | |
|---|---|---|
| WO 90/07907 | 7/1990 | (WO) . |
| WO 6/29927 | 10/1996 | (WO) . |
| WO 96/31155 | 10/1996 | (WO) . |
| WO 97/42903 | 11/1997 | (WO) . |

OTHER PUBLICATIONS

Heathgate Data Corp., "Pulse Oximetry," Jun. 13, 1997, Web Article: HTTP://WWW.HEALTHGATE.COM/HEALTHGATE/FREE/DPH/STATIC/DPH.0200.shtml.

Jobes, et al., "Monitoring of Arterial Hemoglobin Oxygen Saturation Using a Tongue Sensor," Anesthesia & Analgesia, Feb., 1988, vol. 67, pp. 186–188.

O'Leary, et al., "Buccal Pulse Oximeter Is More Accurate Than Finger Pulse Oximeter in Measuring Oxygen Saturation," Anesthesia & Analgesia, Oct., 1992, vol. 75, pp. 495–498.

Cote, et al., "Tongue Oximetry in Children with Extensive Thermal Injury: Comparison with Peripheral Oximetry," Can. Journal Anasth., May, 1992, vol. 39, Issue 5, pp. 454–457.

Reynolds, et al., "Influence of Sensor Site Location on Pulse Oximetry Kinetics in Children," Anesthesia & Analgesia, 1993, vol. 76, pp. 751–754.

* cited by examiner

NASOPHARYNGEAL AIRWAY WITH REFLECTANCE PULSE OXIMETER SENSOR This application claims priority from U.S. provisional Application Ser. No. 60/099,579, filed Sep. 9, 1998 and U.S. provisional Application Ser. No. 60/101,143, filed Sep. 18, 1998.

I. FIELD OF THE INVENTION

The invention relates to the field of reflectance oximetry. More particularly, the invention is directed to a nasopharyngeal airway with a reflectance pulse oximeter sensor.

II. BACKGROUND OF THE INVENTION

With a few exceptions, tradition and technology have favored transillumination pulse oximetry in the operating theater. The principle of operation of the pulse oximeter is fairly simple but is arguably the most important development in anesthesia monitoring in the twentieth century. Two wavelengths of light (usually 660 nm and 940 nm) are used to spectrophotometrically determine the ratio of oxidized to reduced hemoglobin noninvasively as well as to determine the pulsatility of blood plethysmographically. Presently, the most common application of this in the operating theater is via transillumination through the capillary bed of a peripheral digit. However, it is not unusual for multitrauma and thermally injured patients to either have severe peripheral vasoconstriction or to have severely damaged (or missing due to amputation) peripheral vascular beds. Reflectance oximetry rather than transillumination oximetry was the earliest investigative form of the technique. Transillumination pulse oximetry, without question, is the most effective form when oximetry is obtained through skin. However, when skin is not interposed as a barrier to capillary bed access, reflectance pulse oximetry easily can be achieved with very accurate results. The effect is achieved by the backscattering of incident bispectral light that traverses and, on reflection from nonabsorptive collagenous tissues, retraverses formed elements in the blood back to the oximetric detector. Rather than superseding transillumination pulse oximetry, this technique broadens the scope of possible monitoring sites, adding to the clinician's armamentarium.

Conventional pulse oximetry in the severely burned patient can be a significant challenge, yet this monitoring data is vital in operating room and intensive care settings. Most current oximetric approaches depend upon available peripheral sites permitting transillumination oximetry and indeed, this method is sufficient for most surgical conditions and procedures. Unfortunately, patients with severe burns often have few sites for the effective placement of the transilluminating pulse oximeter sensor. In addition, these patients often have severe circulatory compromise rendering the peripheral pulse oximeter less efficient. A variety of studies have shown that central pulse oximeters are more reliably and rapidly responsive than peripheral pulse oximeters.

Reflectance oximetry can be a useful tool where a capillary bed is easily accessible. Indeed, it is used commonly and effectively among intrapartum and neonatal patients whose capillary beds are easily accessed through their skin. The technique has also been applied to adult and pediatric burn patients by placing the reflectance sensor in wounds or over hyperemic sites such as healed partial thickness burns.

The nasal mucosa and the posterior pharynx contain rich capillary beds ideal for reflectance pulse oximetry. Known pulse oximeters are not suitable for use in the nares as they tend to block the nasal passage thus constricting the patient's breathing. In addition, they are prone to difficulties when their electrical components are exposed to liquid, moisture, bodily fluids, and/or surgical fluids. Since they rely on transillumination they also tend to be difficult to hold in place. Accordingly, a need exists for a more convenient device that combines a pulse oximeter sensor with a nasopharyngeal airway.

Nasopharyngeal airways are used in the operating room to establish communication between the nares and the posterior pharynx. Nasopharyngeal airways also are used to perform nasal suctioning.

III. SUMMARY OF THE INVENTION

The invention while addressing the problems of the prior art obtains advantages that were not achievable with the prior art devices.

An object of this invention is to provide an effective device for taking pulse oximetry measurements from nasal and posterior pharyngeal capillary beds.

Another object of the invention is to eliminate the need for employing a separate nasopharyngeal airway when taking pulse oximetry measurements via the nasal cavity.

Another object of the invention is the use of reflectance pulse oximetry via the nasal cavity for a variety of surgical, anesthetic, or critical care procedures performed on patients who are awake, sedated or undergoing general anesthesia.

Another object of the invention is to provide a pulse oximeter in a sealed body that is fluid impermeable.

An advantage of the invention is an improvement in the quality of care resulting from not needing to switch devices or use two separate devices in the nasal cavity.

Another advantage of the invention is improved pulse oximetry readings regardless of the radial position of the device when it is placed in the nares.

Given the following enabling description of the drawings, the apparatus should become evident to a person of ordinary skill in the art.

IV. BRIEF DESCRIPTION OF THE DRAWINGS

V. DETAILED DESCRIPTION OF THE INVENTION

FIGS. 1–5 illustrate a preferred embodiment of the pulse oximeter sensor assembly according to the invention. The pulse oximeter sensor assembly includes a nasopharyngeal airway 10 in combination with pulse oximeter elements 20, 22, 24, and 26. The pulse oximeter sensor elements 20, 22, and 24 are preferably disposed within the wall of the nasopharyngeal airway. Preferably, the wall of the nasopharyngeal airway is made of a clear polymer. Furthermore, it is preferable that the wall may include a thickened section 12 around approximately one-third of the circumferential area to house the pulse oximeter sensor elements 20, 22, and 24.

Alternatively, the thickened section 112 may be around just the elements themselves and not run the length of the wall.

Figure 1:
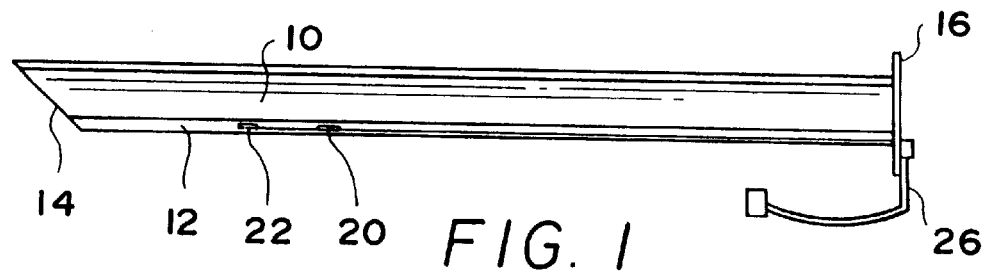
FIG. 1 illustrates a side view of a preferred embodiment.
Figure 4:
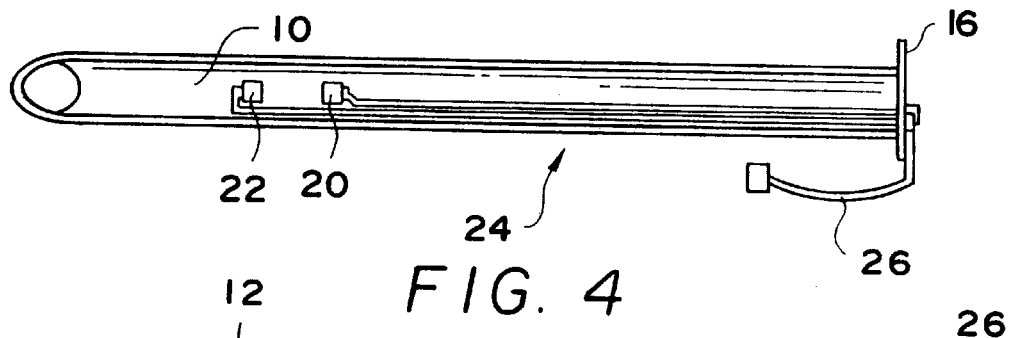
FIG. 4 illustrates a bottom view of the embodiment shown in FIG. 1.
Figure 2:
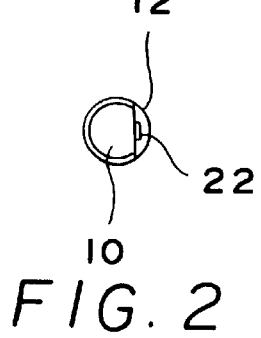
FIG. 2 illustrates a radial cross-section view of the embodiment shown in FIG. 1.
Figure 3:
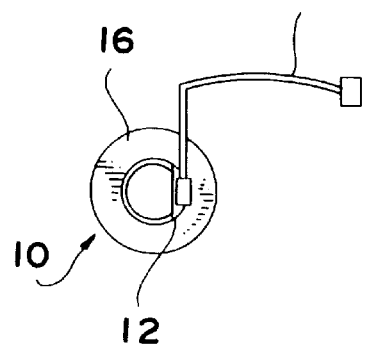
FIG. 3 illustrates a rear view of the embodiment shown in FIG. 1.

As depicted in FIG. 1, the nasopharyngeal airway 10 is preferably a hollow, elongated member defining a passageway, e.g., a cylindrical tubular member, having an insertion end 14 and a base end 16. The insertion end 14 is preferably angled. The base end 16 may be flat and disposed substantially perpendicular to the rest of the nasopharyngeal airway or angled. The base end 16 may include a notch or other marking corresponding to the tip of the nasopharyngeal airway 10 to assist the user in further positioning the device in the patient after insertion of the device.

The pulse oximeter sensor elements 20, 22, and 24 are preferably disposed in the thickened wall section 12 of the nasopharyngeal airway 10. Alternatively, the pulse oximeter sensor elements 20, 22, and 24 may be disposed within the passageway of nasopharyngeal airway 10. The pulse oximeter sensor elements include a light source 20, which preferably emits light with wavelengths of 660 nm (red) and 940 nm (near infrared), a light detector 22 and wiring 24. These pulse oximeter sensor elements are preferably embedded and sealed in the wall of the nasopharyngeal airway with a cover protecting them. Preferably, the cover is a clear, fluid impermeable plastic.

The light source 20 may include more than one emitter. The light source may be one or more of the following: a pair of light emitters such as light emitting diodes (LEDs), a single light emitter, a bispectral emitter, a dual spectral emitter, a photoemitter, a photodiode, or a semiconductor die. However, any light source that facilitates reflectance pulse oximetry may be employed. When the light source 20 is one light emitter then the light emitter, for example, preferably would emit two frequencies of light at about 660 nm and about 940 nm. Typically, the two emitter arrangement will include a red LED near 660 nm and a near-infrared LED emitting in the range of 890 nm to 950 nm. The light source 20 may emit light having a bandwidth in the range of 20 to 50 nm.

A light detector 22 detects light emitted by light source 20. Electrical signals representing the detected light are transmitted by light detector 22 to a spectrophotometer or pulse oximeter that discriminates between the relative intensity of these emissions and provides an index as to the degree of oxygen saturation of hemoglobin in blood. The light detector 22 may be one of the following: a photoelectric receiver, a photodetector, a photodiode receiver, or a semiconductor die.

The wiring 24 connects the pulse oximeter sensor elements to an external cord 26 that may also embedded in the thickened wall section 12 of the nasopharyngeal airway 10. The wiring 24 includes conductive lines and contact electrodes. The light source 20 and the light detector 22 are each connected to their own contact electrode, respectively. The external cord 26 preferably is insulated and connects to the nasopharyngeal airway 10 at the base 16. The external cord 26 has a standard and universal plug design to interface with a pulse monitor, such as a plethysmograph or a pulse oximeter, or other external device. Although not shown, light source 20 and light detector 22 may comprise a wireless pulse oximeter sensor. Preferably, the pulse oximeter sensor elements are used for reflective oximetry as opposed to transillumination oximetry.

Figure 5:
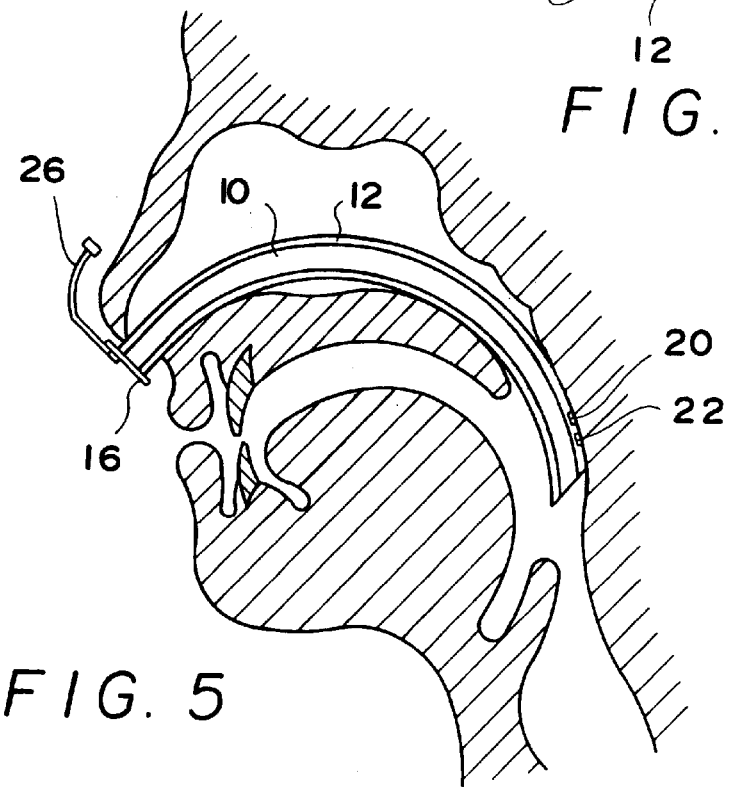
FIG. 5 illustrates the embodiment shown in FIG. 1 in use in a patient.

In accordance with a preferred aspect of the invention, the pulse oximeter sensor elements 20 and 22 may be located near the angled end 14 to facilitate readings taken from the proximal posterior pharynx as shown in FIG. 5. This arrangement provides for easy access and a reliable contact point. However, if the pulse oximeter sensor elements 20 and 22 are located near the base end 16, then the readings will be taken from within the nasal cavity. The nasal cavity provides less reliable and accurate pulse oximetry readings than the posterior pharynx.

In use, the nasopharyngeal airway 10 preferably takes measurements from a central measurement site, namely the proximal posterior pharynx, posterior soft palate or nasal mucosa. The data collected from these locations has proven more reliable then data attainable from periphery locations. The increased reliability is believed to be due to the centrality of the measurement location and the stability of the measurement surfaces. The measurement indicates the oxygen saturation of hemoglobin. Furthermore, the nasopharyngeal airway of this invention is extremely useful in cases where it is difficult at best or not even possible to attach prior art pulse oximeter sensors with clips or straps to the patient. The nasopharyngeal airway of this invention is useful with patients who are critically ill or injured patients including burn or trauma patients without alternative sites and maxillofacial injuries.

The invention is particularly useful when the patient is awake but sedated. However, the invention may be used while the patient is fully awake, during induction of anesthesia, during general anesthesia, on emergence from anesthesia and during recovery. The invention is particularly useful in very wet environments as the oximetric components and wiring are sealed within the polymeric envelope of the nasopharyngeal airway. The invention is useful in field and emergency medical areas in that it can both establish an airway and provide pulse oximetry monitoring in a single device.

The nasopharyngeal airway will preferably be manufactured using polypropylene, polyvinyl chloride, silicones, epoxies, polyester, thermoplastics, rubber, similar flexible material, etc. The material should be sufficiently flexible that it freely bends in accordance with the contour of the nasal passageway. The thickened area is preferably formed from a clear or semi-translucent material to allow for the passage of light from the light source 20 and to the light detector 22.

In keeping with the invention, the pulse oximeter elements may be attached to or disposed adjacent to an internal surface of the passageway. A disposable pulse oximeter like the Nellcor® Oxisensor® II N-25 or D-25 (Nellcor Puritan Bennett®, Inc., Pleasanton, Calif.) may be stripped of its surroundings to leave only the pulse oximeter elements. The pulse oximeter elements may then be feed into the nasopharyngeal airway 10 along one side of the passageway. Even though the pulse oximeter elements and wiring may be present in the passageway, there is sufficient airflow capacity to supply adequate oxygen to the patient.

The method of taking pulse oximeter readings from posterior pharyngeal area within a patient has been submitted to actual testing in the below-described population and according to the following protocol.

The protocol involved comparing posterior pharyngeal reflectance pulse oximetry to conventional peripheral transillumination pulse oximetry in difficult to monitor burn patients. Eight patients' records were reviewed over fourteen consecutive surgical procedures, all consisting of excision and grafting. Patients ranged in age from 9 to 43 years and ranged from 14.5% to 77.5% total body surface area (%TBSA) burned (Mean=30.4, SD [standard deviation]= 22.1). The number of operations per patient ranged from one to four.

A Nellcor® Oxisensor® II pulse oximeter probe was placed in the distal lumen of an appropriately sized oropharyngeal airway with sensor and emitter facing the posterior pharynx. A similar probe was placed on a peripheral digit as a transilluminating pulse oximeter. $SPO_2$ values were noted at five-minute intervals. Concordance statistics as well as a t-test for correlated means were calculated between the simultaneously obtained $SpO_2$ values.

The mean differences between pharyngeal reflectance and peripheral digital transillumination $SpO_2$ values were insignificant for all cases. Concordance statistics were as follows: 0.75 (n=1) and 1.0 (n=12).

Given the near perfect concordance statistics in this study, this data suggests that posterior pharyngeal reflectance oximetry is a simple, highly accurate means of monitoring arterial oxygen saturation in the severely burned patient where oximetric monitoring presents a challenge.

Those skilled in the art will appreciate that various adaptations and modifications of the above-described preferred embodiments can be configured without departing from the scope and spirit of the invention. Therefore, it is to be understood that, within the scope of the appended claims, the invention may be practiced and constructed other than as specifically described herein.

We claim:

1. An oximetry measurement device comprising:
   a base having a hole passing therethrough,
   an elongated member extending from said base, said elongated member having a passageway passing therethrough, the passageway being in communication with the hole of said base, and
   pulse oximeter sensor elements embedded in said elongated member; and
   wherein at least one of said pulse oximeter sensor elements receives light and transmits a signal based on the received light.

2. The device according to claim 1, wherein said elongated member is a cylindrical tube having a wall of non-uniform thickness and said passageway is non-cylindrical.

3. The device according to claim 2, wherein the wall includes a first section and a second section, the second section being thicker than the first section and the pulse oximeter sensor elements being embedded in the second section.

4. The device according to claim 1, wherein said pulse oximeter sensor elements include:
   a light source, and
   a light detector in communication with the light source.

5. The device according to claim 4, wherein said light source includes one of at least one light emitter, a bispectral emitter, a dual spectral emitter, at least one photoemitter, at least one photodiode, at least one light emitting diode, and a semiconductor die.

6. The device according to claim 4, wherein said at least one light detector includes one of a photoelectric receiver, a photodetector, a photodiode receiver, and a semiconductor die.

7. The device according to claim 1, wherein said pulse oximeter sensor elements include:
   means for transmitting light, and
   means for receiving light transmitted by said means for transmitting light.

8. A method for taking oximetry readings from a posterior pharyngeal region of a patient, said method comprising:
   coupling the device recited in claim 1 to a pulse oximeter,
   inserting the elongated member of the device recited in claim 1 through a nasal cavity of the patient,
   aligning the pulse oximeter sensor elements of the device according to claim 1 with the posterior pharyngeal region of the patient, and
   contacting the pulse oximeter sensor elements of the device according to claim 1 with the posterior pharyngeal region of the patient.

9. A device according to claim 1, wherein said elongated member is made from flexible material and said flexible material includes a portion capable of transmitting light, and said light transmitting portion is spaced from said base.

10. A method for taking oximetry readings from a nasal mucosa of a patient, said method comprising:
    coupling the device recited in claim 1 to a pulse oximeter,
    inserting the elongated member of the device recited in claim 1 through a nasal cavity of the patient,
    aligning the pulse oximeter sensor elements of the device according to claim 1 with the nasal mucosa of the patient, and
    contacting the pulse oximeter sensor elements of the device according to claim 1 with the nasal mucosa of the patient.

11. A device comprising:
    a base having a hole passing therethrough,
    an elongated member extending from said base, said part having a passageway passing therethrough, wherein the passageway being in communication with the hole of said base, and
    pulse oximeter sensor elements disposed in the passageway; and
    wherein at least one of said pulse oximeter sensor elements receives light and transmits a signal based on the received light.

12. The device according to claim 11, wherein said elongated member is a cylindrical tube.

13. The device according to claim 11, wherein the wall includes a first section and a second section, the second section being thicker than the first section and the pulse oximeter sensor elements being embedded in the second section.

14. The device according to claim 11, wherein said pulse oximeter sensor elements include:
    a light source, and
    a light detector in communication with the light source.

15. The device according to claim 14, wherein said light source includes one of at least one light emitter, a bispectral emitter, a dual spectral emitter, at least one photoemitter, at least one photodiode, at least one light emitting diode, and a semiconductor die.

16. The apparatus according to claim 14, wherein said at least one light detector includes one of a photoelectric receiver, a photodetector, a photodiode receiver, and a semiconductor die.

17. The device according to claim 11, wherein said pulse oximeter sensor elements include:
    means for transmitting light, and
    means for receiving light transmitted by said means for transmitting light.

18. A method for taking oximetry readings from a posterior pharyngeal region of a patient, said method comprising:
    coupling the device recited in claim 11 to a pulse oximeter,
    inserting the elongated member of the device recited in claim 11 through a nasal cavity of the patient, aligning the pulse oximeter sensor elements of the device according to claim 11 with the posterior pharyngeal region of the patient, and contacting the pulse oximeter sensor elements of the device according to claim 11 with the posterior pharyngeal region of the patient.

19. A device according to claim 11, wherein said elongated member is made from flexible material and said flexible material includes a portion capable of transmitting light and said light transmitting portion is spaced from said base.

20. A method for taking oximetry readings from a nasal mucosa of a patient, said method comprising:

coupling the device recited in claim 11 to a pulse oximeter, inserting the elongated member of the device recited in claim 11 through a nasal cavity of the patient, aligning the pulse oximeter sensor elements of the device according to claim 11 with the nasal mucosa of the patient, and contacting the pulse oximeter sensor elements of the device according to claim 11 with the nasal mucosa of the patient.

\* \* \* \* \*

UNITED STATES PATENT AND TRADEMARK OFFICE
CERTIFICATE OF CORRECTION

PATENT NO. : 6,266,547 B1
DATED : July 24, 2001
INVENTOR(S) : Walker et al.

It is certified that error appears in the above-identified patent and that said Letters Patent is hereby corrected as shown below:

Claim 11,
Line 3, change "part" to -- elongated member --.

Signed and Sealed this

Sixteenth Day of April, 2002

Attest:

JAMES E. ROGAN
Attesting Officer          Director of the United States Patent and Trademark Office